US012708483B2

(12) United States Patent
Tadano et al.

(10) Patent No.: US 12,708,483 B2
(45) Date of Patent: Aug. 18, 2026

(54) SURGERY ASSISTING DEVICE AND COMPUTING DEVICE FOR SURGERY ASSISTING DEVICE

(71) Applicant: RIVERFIELD INC., Tokyo (JP)

(72) Inventors: Kotaro Tadano, Tokyo (JP); Masao Kanazawa, Tokyo (JP); Hiroki Kayasuga, Tokyo (JP); Masataka Suzuki, Tokyo (JP); Teruyuki Nishihara, Tokyo (JP)

(73) Assignee: RIVERFIELD INC., Tokyo (JP)

( * ) Notice: Subject to any disclaimer, the term of this patent is extended or adjusted under 35 U.S.C. 154(b) by 555 days.

(21) Appl. No.: 18/119,122

(22) Filed: Mar. 8, 2023

(65) Prior Publication Data

US 2023/0218366 A1 Jul. 13, 2023

Related U.S. Application Data

(63) Continuation of application No. PCT/JP2020/034138, filed on Sep. 9, 2020.

(51) Int. Cl.

| | |
|---|---|
| ***A61B 90/50*** | (2016.01) |
| ***A61B 46/10*** | (2016.01) |
| *A61B 34/20* | (2016.01) |

(52) U.S. Cl.

CPC .............. *A61B 90/50* (2016.02); *A61B 46/10* (2016.02); *A61B 2034/2055* (2016.02); *A61B 2034/2059* (2016.02)

(58) Field of Classification Search

CPC .... A61B 2034/2055; A61B 2034/2059; A61B 2090/061; A61B 2090/067; A61B 34/30; A61B 46/10; A61B 90/50

See application file for complete search history.

(56) References Cited

U.S. PATENT DOCUMENTS 5,228,429 A 7/1993 Hatano
7,684,898 B2 * 3/2010 Pagel .................... B25J 9/1692 700/254
2008/0010705 A1 * 1/2008 Quaid .................... A61B 34/20 600/407
2008/0177285 A1 * 7/2008 Brock .................... A61B 34/71 606/1
2015/0100069 A1 4/2015 Inoue et al.
2016/0100899 A1 4/2016 Jinno et al.
(Continued)

FOREIGN PATENT DOCUMENTS

JP 4-95002 U 8/1992
JP 6-63003 A 3/1994
(Continued)

OTHER PUBLICATIONS

International Search Report for PCT/JP2020/034138 dated Dec. 1, 2020.
Written Opinion for PCT/JP2020/034138 dated Dec. 1, 2020.

*Primary Examiner* — Scott Luan
(74) *Attorney, Agent, or Firm* — Sughrue Mion, PLLC

(57) ABSTRACT

A surgery assisting device that includes one or more joint portions and that holds a surgical instrument, and a computing device that obtains angle information of a joint portion of the one or more joint portions in a state in which a distal end of the surgical instrument is positioned at a predetermined position and determines a length of the surgical instrument based on the angle information.

20 Claims, 12 Drawing Sheets

(56) References Cited

U.S. PATENT DOCUMENTS

| | | | | |
|---|---|---|---|---|
| 2017/0165013 | A1* | 6/2017 | Itkowitz | A61B 34/37 |
| 2019/0298460 | A1 | 10/2019 | Al-Jadda et al. | |

FOREIGN PATENT DOCUMENTS

| | | | |
|---|---|---|---|
| JP | 2003-284726 | A | 10/2003 |
| JP | 2014-8374 | A | 1/2014 |
| JP | 2014-008374 | A | 1/2014 |
| JP | 2015-228922 | A | 12/2015 |
| WO | 2014/199414 | A1 | 12/2014 |

* cited by examiner

SURGERY ASSISTING DEVICE AND COMPUTING DEVICE FOR SURGERY ASSISTING DEVICE

CROSS REFERENCE TO RELATED APPLICATION

This U.S. Application is a continuation application of International Application No. PCT/JP2020/034138 filed Sep. 9, 2020, in the Japanese Patent Office, the contents of which being incorporated by reference herein in its entirety.

BACKGROUND

The present disclosure relates to a computing device that performs a computation regarding a surgery assisting device configured to be able to hold a surgical instrument, and in particular, relates to a technique for determining a length of the surgical instrument held by the surgery assisting device by a computation.

In recent years, surgical operations using a surgery assisting device is spreading. In a surgery assisting device, different surgical instruments or tools may be used and may be inserted into a patient undergoing a surgical procedure. As such, it is advantageous to identify where a distal end of the surgical instrument is positioned to better control the surgical instrument during the surgical procedure.

SUMMARY

It is an aspect to achieve an improved degree of freedom of a usable surgical instrument without requiring a use of a jig.

According to an aspect of one or more embodiments, there is provided a surgery assisting device comprising an arm including one or more joint portions and configured to hold a surgical instrument; and a computing device configured to obtain angle information of at least one joint portion of the one or more joint portions in a state in which a distal end of the surgical instrument is positioned at a predetermined position and determine a length of the surgical instrument based on the angle information.

According to another aspect of one or more embodiments, there is provided a computing device for a surgery assisting device that is configured to hold a surgical instrument on a distal end portion of the surgery assisting device and that includes an arm portion including one or more joint portions, the computing device comprising a microcomputer that obtains angle information of at least one joint portion of the one or more joint portions in a state in which a distal end of the surgical instrument held by the arm portion is positioned at a predetermined position and that determines a length of the surgical instrument by based on the angle information.

BRIEF DESCRIPTION OF DRAWINGS

The above and/or other aspects will become apparent and more readily appreciated from the following description of exemplary embodiments, taken in conjunction with the accompanying drawings in which.

DETAILED DESCRIPTION

Figure 1:
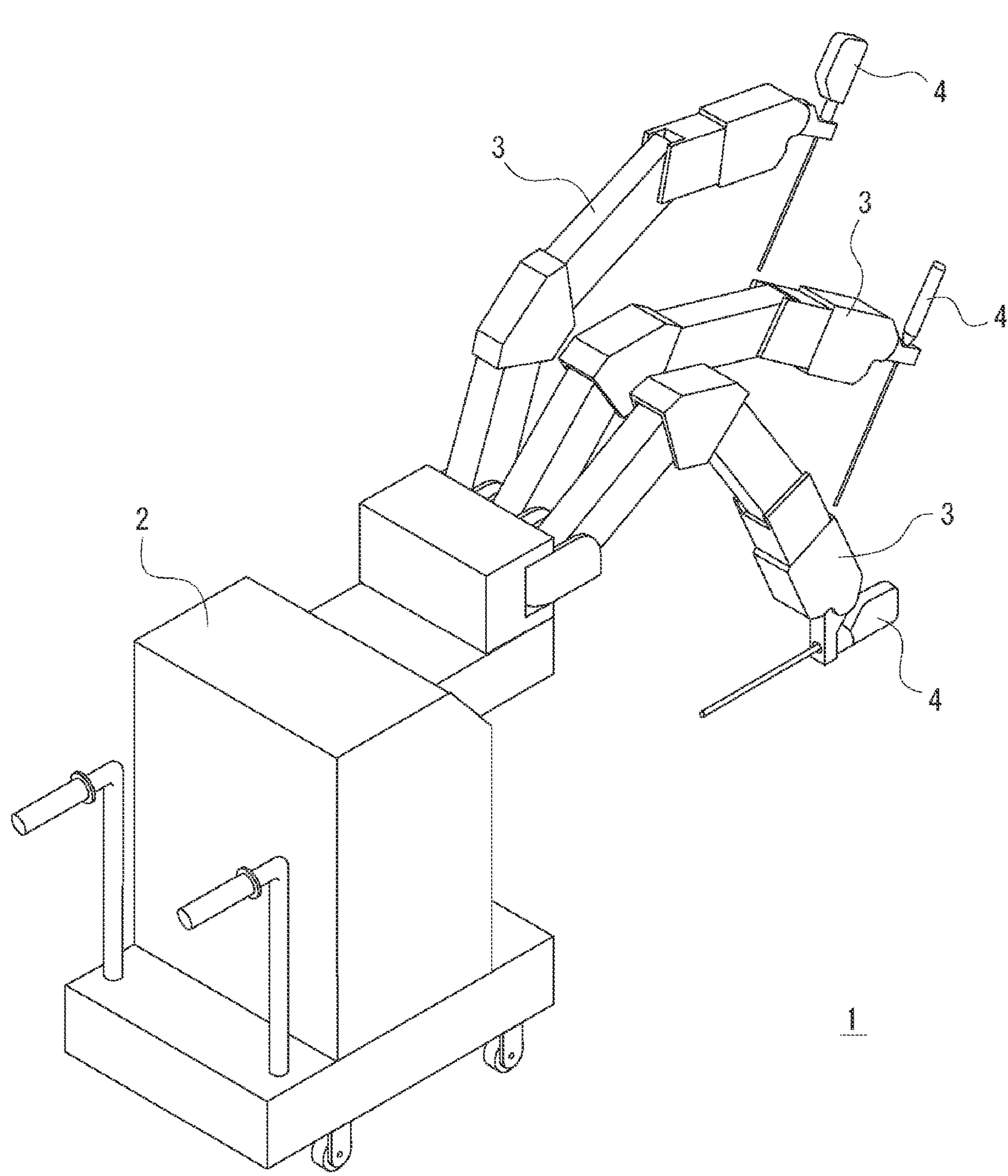
FIG. 1 is a perspective view illustrating a schematic external configuration of a surgery assisting device according to some embodiments.

A surgery assisting device may include a movable body as a plurality of arm portions for changing the position and the posture of the surgical instrument as well as for holding the surgical instrument, such as an endoscope and a forceps.

In a surgery assisting device, an arm portion is configured to have one or a plurality of joint portions so as to at least freely bend, and thus, are configured to be able to change positions and postures of a surgical instrument held by a distal end portion.

In the surgery assisting device, when the position and the posture of the surgical instrument are changed, the surgery assisting device is configured to perform a control computation for identifying where the distal end of the surgical instrument is positioned and controlling the arm portion. In this respect, the length of the surgical instrument is an important parameter in identifying the distal end position of the surgical instrument. In particular, a scope (an endoscope) as a surgical instrument falls into the category of long surgical instruments, and therefore, it is important to know the length parameter.

Some related art surgery assisting devices employ a method in which only an exclusive item specialized for the surgery assisting device is usable for a surgical instrument as a scope so as to guarantee a constant length of the scope used in the control computation.

This method, however, has a disadvantage in that a latest surgical instrument manufactured by another company is no longer usable.

There is another disadvantage with this method in that the method also leads to an increased cost (introduction cost) in introducing the surgery assisting device. That is, a hospital or the like that performs a laparoscopic surgery and the like may have already possessed a scope for surgery, and the scope can no longer be used for the surgery assisting device in such a case, which means there arises a necessity to additionally purchase a scope exclusive for the surgery assisting device, thereby leading to an increased introduction cost.

Some related art surgery assisting devices employ a method that keeps the length of the scope constant using a jig. Specifically, a jig for adjusting a distance from a distal end of the scope to a holding point by the arm portion is mounted on the scope, and the length of the scope (in this case, the length from the holding point to the distal end) is adjusted to a constant length by the jig.

However, this method needs to sterilize the jig when the jig is allowed to be reused. When the jig is disposable, it is necessary to prepare a new jig for each use, which leads to a cost increase.

It is thus an aspect to achieve an improved degree of freedom of a usable surgical instrument without requiring a use of a jig.

A computing device according to some embodiments may be used for a surgery assisting device that is configured to hold a surgical instrument on a distal end portion and includes a freely bendable arm portion by including one or a plurality of joint portions. The computing device includes a computing unit that obtains angle information of the joint portions in a state where a distal end of the surgical instrument held by the arm portion is positioned at a predetermined position and determines a length of the surgical instrument by a geometric computation using the angle information.

When the condition that the distal end of the surgical instrument is positioned at the predetermined position is imposed, the angles of the joint portions also change if the length of the surgical instrument differs. Therefore, under the condition that the distal end of the surgical instrument is positioned at the predetermined position as described above, it is possible to appropriately determine the length of the surgical instrument by the geometric computation by obtaining the angle information of the joint portions.

The computing device according to some embodiments may have a configuration in which the predetermined position is a position in air.

This configuration eliminates the need for bringing the distal end of the surgical instrument into contact with an object in determining the length of the surgical instrument.

The computing device according to some embodiments may have a configuration in which as the joint portions, a first joint portion, a second joint portion, and a third joint portion are arranged in an order from a base side to a distal end side of the arm portion, and the computing unit determines the length of the surgical instrument by: obtaining angle information of the first joint portion and angle information of the second joint portion in a state where the distal end of the surgical instrument is positioned at the predetermined position; and performing a computation based on a trigonometric function using the obtained angle information of the first joint portion and angle information of the second joint portion, a length of a link portion between the first joint portion and the second joint portion, and a length of a link portion between the second joint portion and the third joint portion.

This configuration ensures determining the length of the surgical instrument corresponding to the case where the arm portion includes three or more joint portions.

The computing device according to some embodiments may have a configuration in which the arm portion includes a surgical instrument holding portion positioned at a distal end portion of the arm portion and configured to hold the surgical instrument, a distal end joint portion as the joint portion to which the surgical instrument holding portion is coupled, and a light emitting portion disposed in a link portion in an arm base side of the distal end joint portion and emits a guide light that guides a position of the distal end of the surgical instrument toward an outward direction of the link portion, the computing unit determines the length of the surgical instrument by obtaining angle information of the distal end joint portion in a state where the distal end of the surgical instrument is positioned at the position where the guide light guides and performing a geometric computation using the angle information.

Since the distal end of the surgical instrument is guided which position to be positioned for determining the length of the surgical instrument, it is easy for a user to adjust the distal end position of the surgical instrument to the predetermined position.

The computing device according to some embodiments may have a configuration in which the computing unit determines the length of the surgical instrument by performing a computation based on a trigonometric function using the obtained angle information of the distal end joint portion, a length of a perpendicular line to an optical axis of the guide light from a joint shaft of the distal end joint portion, and a length from the joint shaft of the distal end joint portion to a base position of the surgical instrument.

This configuration ensures appropriately determining the length of the surgical instrument when the method of emitting the guide light from the light emitting portion disposed in the link portion in the arm base side of the distal end joint portion is employed.

The computing device according to some embodiments may have a configuration in which the predetermined position is a position covered by a drape in the surgery assisting device.

This configuration ensures bringing the distal end of the surgical instrument into contact with the surgery assisting device over the sterilized drape when the length of the surgical instrument is determined.

The computing device according to some embodiments may have a configuration in which the computing unit performs a computation to determine the length of the surgical instrument according to an operation to a predetermined operator disposed in the surgery assisting device.

The above-described predetermined operator can be functioned as an operator for notifying the device side of the completion of the positioning of the distal end of the surgical instrument to the predetermined position, and the above-described configuration ensures appropriately performing the computation to determine the length of the surgical instrument in response to the completion of the positioning.

Various embodiments may ensure achieving an improved degree of freedom of a usable surgical instrument without requiring a use of a jig for a surgery assisting device.

The following describes surgery assisting devices as embodiments in the order below.

[Overview of Surgery Assisting Device]

Embodiments exemplarily describe surgery assisting devices of a type installed on a floor or the like of an operating room and used. However, embodiments are not limited to those of the type installed on a floor or the like of an operating room and used, and various surgery assisting devices, such as those of a type mounted on a ceiling or a wall surface of an operating room and used, are also applicable.

FIG. 1 illustrates an example of a surgery assisting device 1 according to some embodiments.

As illustrated, the surgery assisting device 1 includes a base portion 2 and a plurality of arm portions 3.

The base portion 2 is a portion placed on a floor or the like of an operating room and serves as a supporting portion of each of the arm portions 3.

The arm portions 3 have respective distal end portions on which surgical instruments 4 can be held and are possible to change the positions and the postures of the surgical instruments held by the distal end portions with their own movements.

As illustrated, the surgery assisting device 1 of this example includes three arm portions 3. Of these arm portions 3, the arm portion 3 positioned in the center is the arm portion 3 that holds a scope (an endoscope) as the surgical instrument 4. Other arm portions 3 can be used as the arm portions 3 that hold the surgical instruments 4 other than the scope, such as forceps.

Note that, the number of the arm portion 3 is not limited to three, and may be one or plural.

Figure 2:
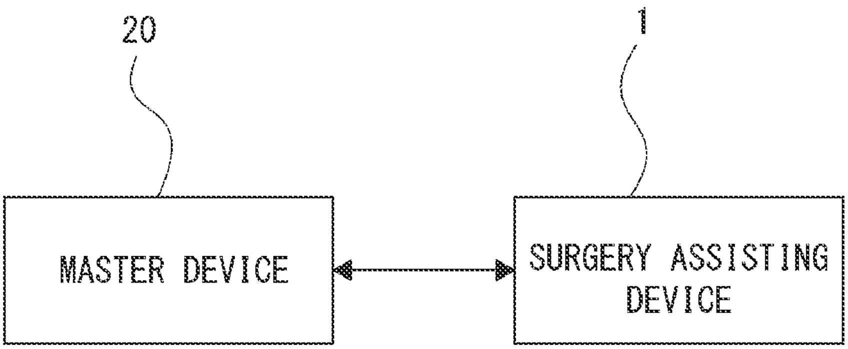
FIG. 2 is a drawing illustrating a configuration overview of a surgery assisting system including the surgery assisting device of FIG. 1, according to some embodiments.

FIG. 2 is a drawing illustrating a configuration overview of a surgery assisting system including the surgery assisting device 1, according to some embodiments.

As illustrated, the surgery assisting system includes the surgery assisting device 1 and a master device 20. The master device 20 includes various operators for operating the surgery assisting device 1 and functions as an operating device of the surgery assisting device 1.

The surgery assisting device 1 and the master device 20 are configured to be able to mutually communicate data through wire or wirelessly. The master device 20 generates a control signal for controlling the movements of the arm portions 3 based on operation input information from a user (for example, a surgeon, such as a doctor) and transmits the control signal to the surgery assisting device 1. The surgery assisting device 1 controls the movements of the arm portions 3 based on the control signal.

This configuration achieves a surgery assisting system that can remotely control the positions and the postures of the plurality of surgical instruments 4 to perform a surgical operation.

[Schematic Configuration of Arm Portion]

Figure 3:
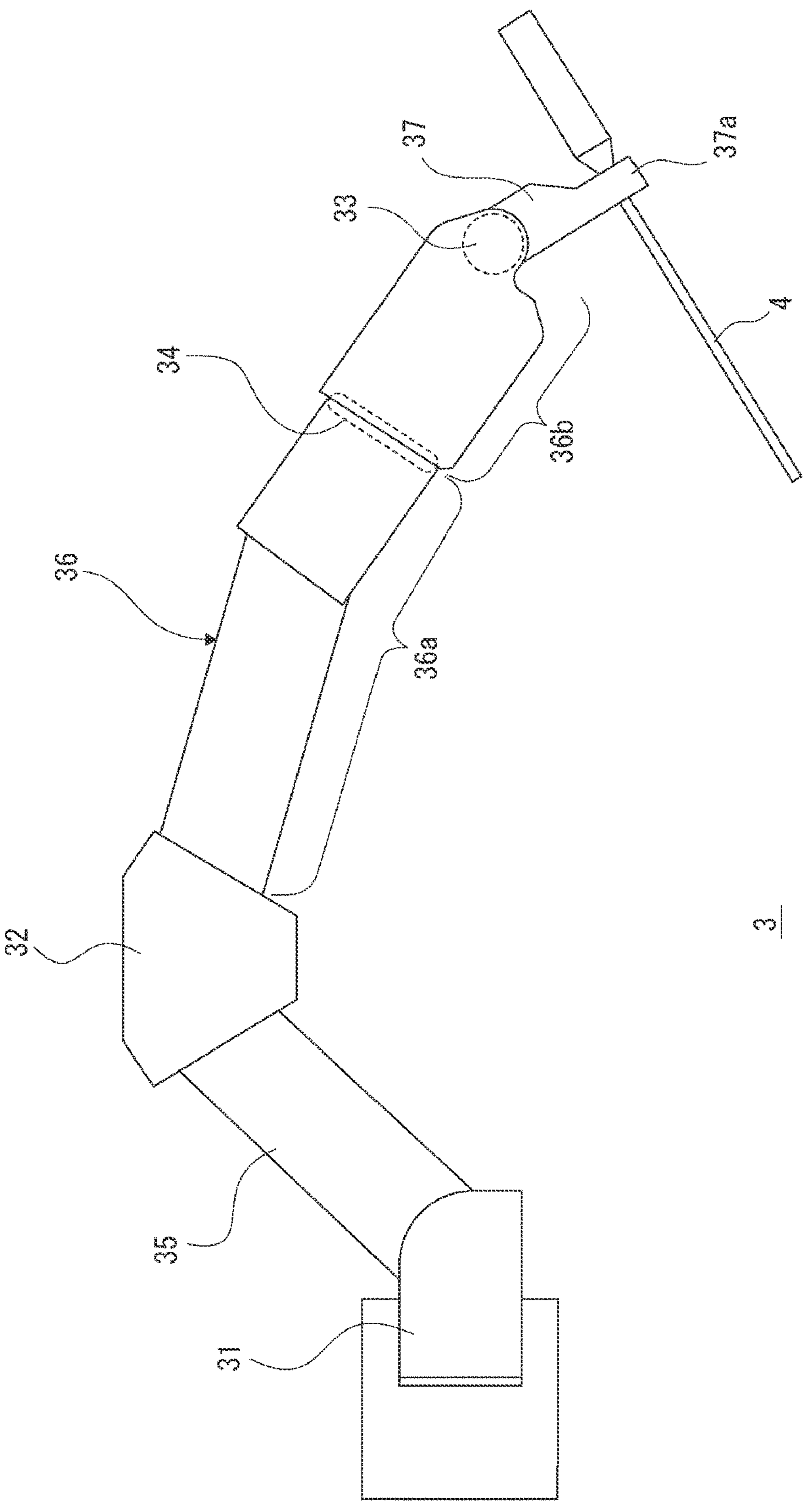
FIG. 3 is a drawing for describing an exemplary schematic configuration of an arm portion, according to some embodiments.

FIG. 3 is a drawing for describing an exemplary schematic configuration of the arm portion 3, according to some embodiments.

As illustrated, the arm portion 3 includes a first joint portion 31, a second joint portion 32, a third joint portion 33, a rotary joint portion 34, a first link portion 35, a second link portion 36, and a surgical instrument holding portion 37.

The first joint portion 31, the second joint portion 32, and the third joint portion 33 are arranged in this order from an arm base side to an arm distal end side. The first link portion 35 is a portion that connects (links) the first joint portion 31 to the second joint portion 32, and the second link portion 36 is a portion that connects between the second joint portion 32 and the third joint portion 33. The arm distal end side of the third joint portion 33 is coupled to the surgical instrument holding portion 37 configured to be able to hold the surgical instrument 4. As illustrated, the surgical instrument holding portion 37 includes a holding mechanism 37*a* for removably holding the surgical instrument 4 on the portion that is the most distal end side of the arm.

Each of the first joint portion 31, the second joint portion 32, and the third joint portion 33 is a joint portion for bending the arm portion 3 and has a turning shaft parallel in a depth direction when the arm portion 3 is viewed edge-on as illustrated.

The first joint portion 31, second joint portion 32, and third joint portion 33 have an actuator (a motor in this example) for turning the respectively corresponding link portions.

The first joint portion 31 is supported by the base portion 2 illustrated in FIG. 1 and turnably supports the first link portion 35. The second joint portion 32 is supported by the first link portion 35 and turnably supports the second link portion 36, and the third joint portion 33 is supported by the second link portion 36 and turnably supports the surgical instrument holding portion 37.

In this example, the second link portion 36 is divided into a second link front portion 36*a* supported by the second joint portion 32 and a second link distal portion 36*b* positioned in the arm distal end side with respect to the second link front portion 36*a*. The rotary joint portion 34 is positioned between the second link front portion 36*a* and the second link distal portion 36*b*, has a rotation shaft parallel in a direction perpendicular to a division surface between the second link front portion 36*a* and the second link distal portion 36*b* (that is, a direction perpendicular to a cross-sectional surface when the second link portion 36 is cut in a depth direction on the paper), and rotatably supports the portion that is the arm distal end side from the second link distal portion 36*b* with the rotation shaft as the rotational center.

Note that, the rotary joint portion 34 is not necessarily disposed. That is, in some embodiments, the rotary joint portion 34 may be omitted.

While this example exemplarily describes the case where three joint portions, the first joint portion 31, the second joint portion 32, and the third joint portion 33, for bending the arm portion 3 are disposed, the number of the joint portions may be one or plural.

[Schematic Internal Configuration of Surgery Assisting Device]

Figure 4:
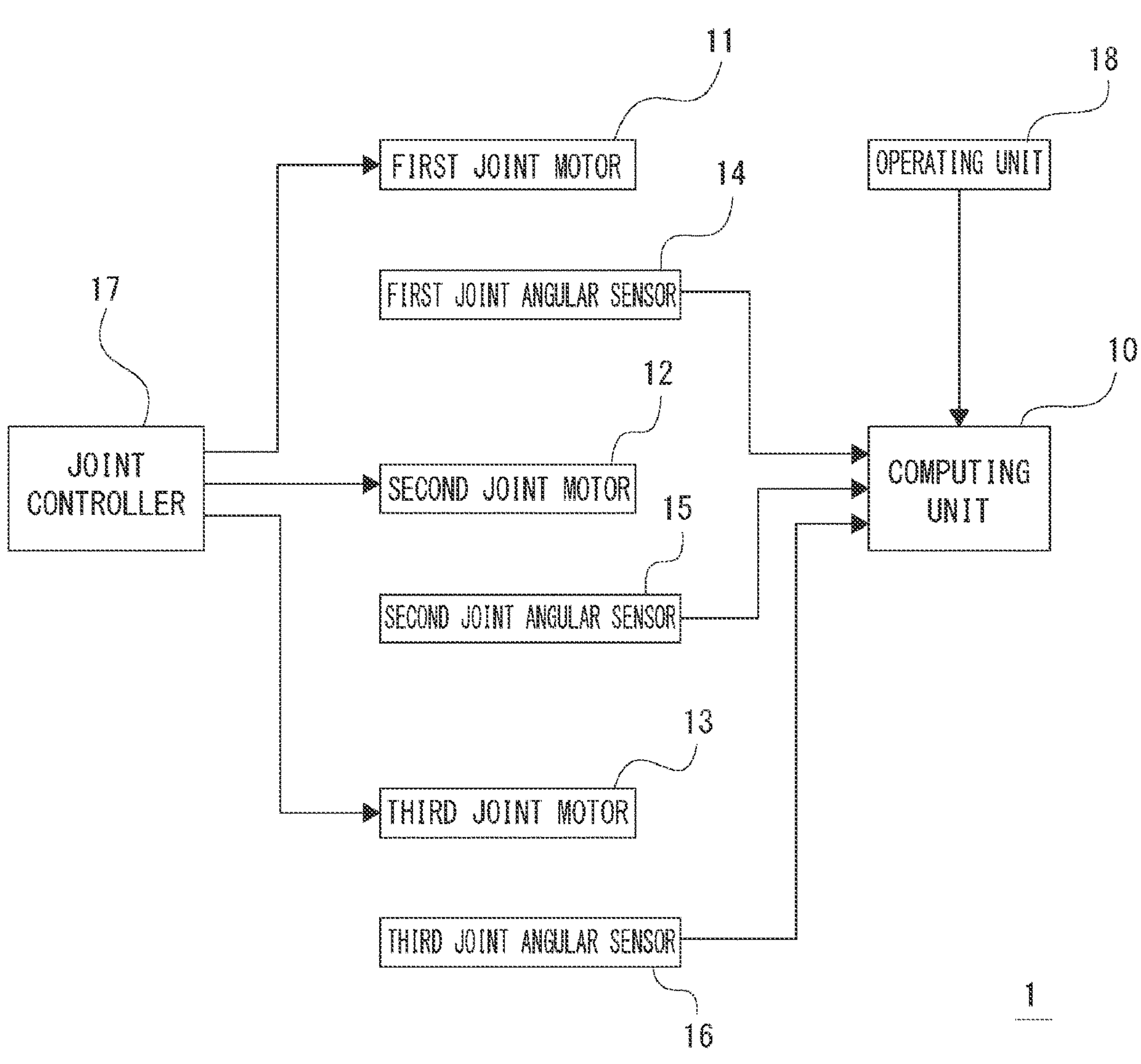
FIG. 4 is a block diagram illustrating an exemplary schematic internal configuration of the surgery assisting device, according to some embodiments.

FIG. 4 is a block diagram illustrating an exemplary schematic internal configuration of the surgery assisting device 1, according to some embodiments.

As illustrated, the surgery assisting device 1 includes a computing unit 10, a first joint motor 11, a second joint motor 12, a third joint motor 13, a first joint angular sensor 14, a second joint angular sensor 15, a third joint angular sensor 16, a joint controller 17, and an operating unit 18.

The first joint motor 11, the second joint motor 12, and the third joint motor 13 are motors for driving the first joint portion 31, the second joint portion 32, and the third joint portion 33, respectively.

The first joint angular sensor 14, the second joint angular sensor 15, and the third joint angular sensor 16 are sensors that detect joint angles of the first joint portion 31, the second joint portion 32, and the third joint portion 33, respectively.

The joint angle means a turning angle of the link portion supported by the joint portion. The first joint angular sensor 14, the second joint angular sensor 15, and the third joint angular sensor 16 have sensors that detect rotation angles of the first joint motor 11, the second joint motor 12, and the third joint motor 13, respectively and detect joint angles of the first joint portion 31, the second joint portion 32, and the third joint portion 33 based on the detected rotation angles of the motors.

The joint controller 17 drivingly controls the first joint motor 11, the second joint motor 12, and the third joint motor 13 to control the bending movement of the arm portion 3. That is, the joint controller 17 controls the position and the posture of the surgical instrument 4 held by the arm portion 3.

While the illustration is omitted, the joint controller 17 is supplied with the control signal generated by the master device 20 illustrated in FIG. 2 based on an operation input by a user, such as a surgeon. The joint controller 17 drivingly controls the first joint motor 11, the second joint motor 12, and the third joint motor 13 based on the control signal.

The computing unit 10 is configured as a computing device, such as a microcomputer including a Central Processing Unit (CPU), a Read Only Memory (ROM), and a Random Access Memory (RAM).

The information of the joint angles detected by the first joint angular sensor 14, the second joint angular sensor 15, and the third joint angular sensor 16 are input to the computing unit 10. The operation input information from the operating unit 18 is input to the computing unit 10.

The operating unit 18 is a comprehensive representation of various operators (not illustrated), such as buttons, keys, dials, and a touchscreen, disposed on the surgery assisting device 1. In other words, the operating unit 18 is an input device such as one or more of a keyboard, microphone, joystick, touchpad, trackpad, etc. that are provided on the surgery assisting device 1 for inputting information into the surgery assisting device 1. The operating unit 18 outputs the operation input information corresponding to the input operation by a user to the computing unit 10, and the computing unit 10 executes a process corresponding to the operation input information to achieve the operation of the surgery assisting device 1 corresponding to the input operation by the user.

The computing unit 10 performs a computation to determine a length of the surgical instrument 4 based on the operation input information from the operating unit 18 and the information of the joint angle detected by at least any of the first joint angular sensor 14, the second joint angular sensor 15, and the third joint angular sensor 16. Specifically, the computing unit 10 in this example performs the computation to determine the length of the surgical instrument 4 based on the information of the joint angle of the first joint portion 31 detected by the first joint angular sensor 14 and the information of the joint angle of the second joint portion 32 detected by the second joint angular sensor 15 as described later.

Note that the surgery assisting device 1 of this example actually includes a motor (an actuator) for driving the rotary joint portion 34 and an angular sensor, which are not illustrated here. The joint controller 17 also drivingly controls a motor for driving the rotary joint portion 34 based on the control signal from the master device 20 in practice.

[Computation of Surgical Instrument Length]

Figure 5:
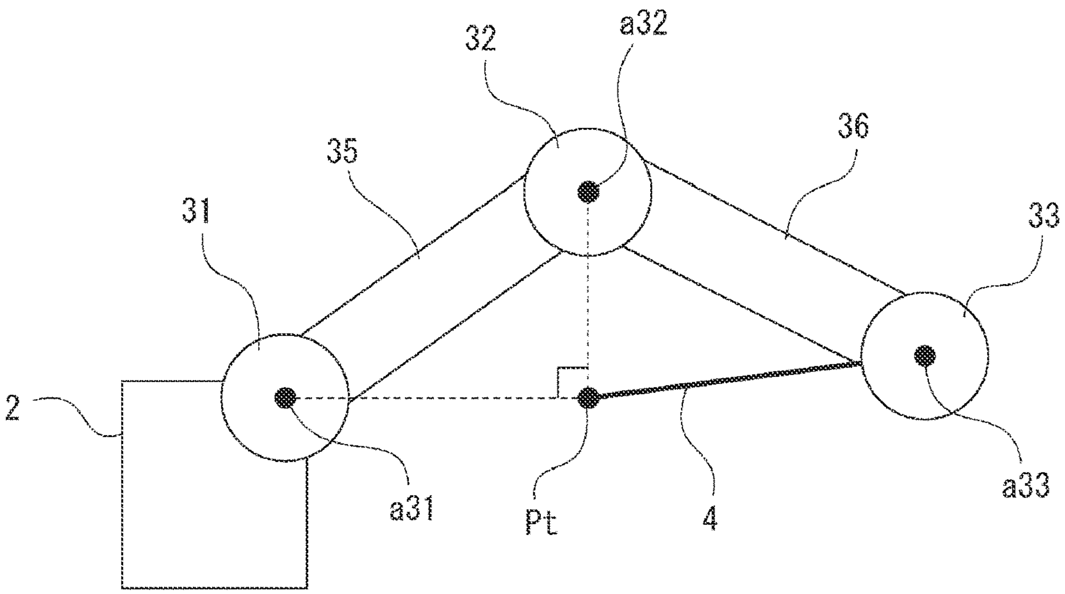
FIG. 5 is a drawing schematically illustrating a configuration of a surgery assisting device, according to some embodiments.
Figure 6:
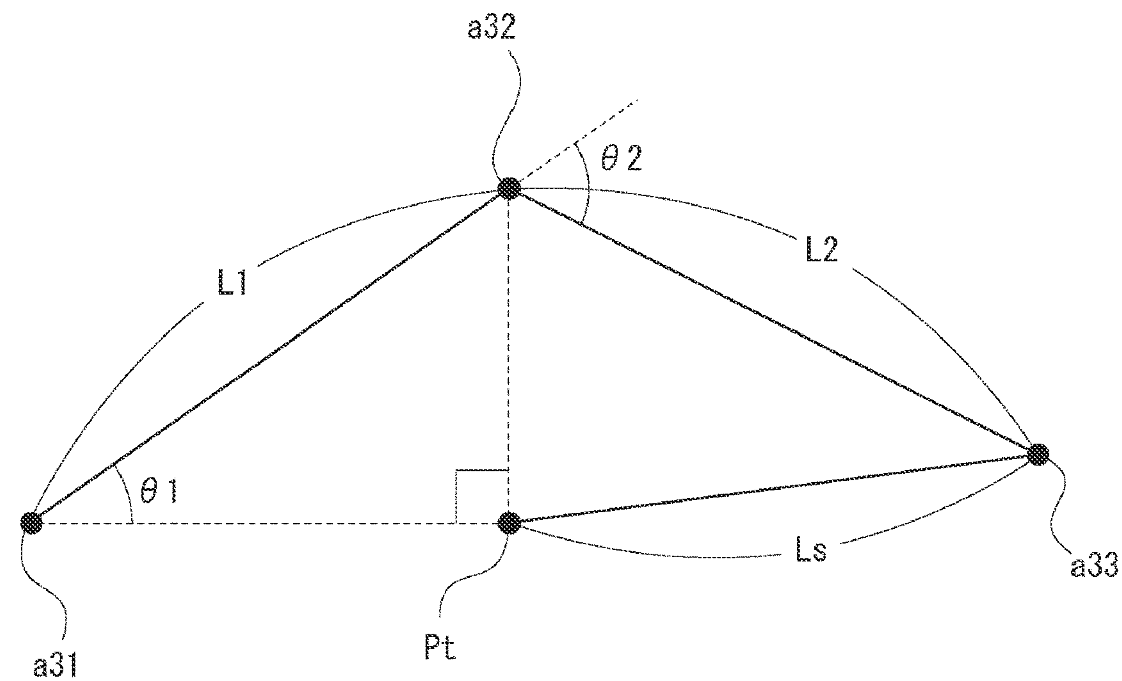
FIG. 6 is an explanatory drawing for a computation method of a length of a surgical instrument, according to some embodiments.

With reference to FIG. 5 and FIG. 6, a method for determining the length of the surgical instrument 4 according to some embodiments will be described. Here, the surgical instrument 4 is described as a scope by way of illustration.

FIG. 5 is a drawing schematically illustrating a configuration of the surgery assisting device 1 according to some embodiments, and specifically, schematically illustrating a relationship between the first joint portion 31, the second joint portion 32, and the third joint portion 33, the first link portion 35, and the second link portion 36, and the surgical instrument 4 in the surgery assisting device 1, according to some embodiments.

In some embodiments, a condition is set to position the distal end of the surgical instrument 4 to a predetermined position Pt determined in advance when the length of the surgical instrument 4 is determined. In this example, the predetermined position Pt may be set as a position in air. Specifically, the predetermined position Pt in this case may be set to be a position of an intersection point between a horizontal line passing through the turning shaft a31 of the first joint portion 31 and a perpendicular line drawn from a turning shaft a32 of the second joint portion 32 to the horizontal line as illustrated.

The turning shaft of the joint portion is hereinafter described as a "joint shaft," and the turning shaft a31 of the first joint portion 31 is described as a "joint shaft a31" and a turning shaft a32 of the second joint portion 32 is described as a "joint shaft a32." A turning shaft a33 of the third joint portion 33 illustrated in the drawing is described as a "joint shaft a33."

In determining the length of the surgical instrument 4, first, a user is caused to manually operate the arm portion 3 to position the distal end of the surgical instrument 4 to the predetermined position Pt. The computing unit 10 obtains the angle information of the joint portion in the state where the distal end of the surgical instrument 4 is thus positioned at the predetermined position Pt and determines the length of the surgical instrument 4 by a computation based on a trigonometric function using the angle information.

FIG. 6 is an explanatory drawing for a computation method of the length of the surgical instrument 4 according to some embodiments and illustrates points that indicate the joint shaft a31 of the first joint portion 31, the joint shaft a32 of the second joint portion 32, the joint shaft a33 of the third joint portion 33, and the predetermined position Pt and straight lines connecting these points.

The angle formed by the straight line connecting the joint shaft a31 to the joint shaft a32 and the straight line connecting the joint shaft a31 to the predetermined position Pt as illustrated is "θ1." An exterior angle of a corner portion formed by the straight line connecting the joint shaft a31 to the joint shaft a32 and the straight line connecting the joint shaft a32 to the joint shaft a33 is "θ2."

Furthermore, a length of the straight line connecting the joint shaft a31 to the joint shaft a32 is "L1," and a length of the straight line connecting the joint shaft a32 to the joint shaft a33 is "L2." Here, these lengths L1, L2 are known values as a length of the first link portion 35 and a length of the second link portion 36, respectively.

The length of the surgical instrument 4 to be determined, that is, a length of the straight line connecting the joint shaft a33 to the predetermined position Pt is "Ls" in this example.

When the angles θ1 and θ2 and the lengths L1 and L2 are defined as described above, the length Ls of the surgical instrument 4 can be determined based on the following [Formula 1] by the law of cosines.

$$Ls^2 = \{L1 \cdot \sin\theta1\}^2 + L2^2 - 2L1 \cdot L2 \cdot \sin\theta1 \cdot \cos\left(\frac{\pi}{2} + \theta1 - \theta2\right) \quad \text{[Formula 1]}$$

The angles θ1 and θ2 can be determined based on the joint angle of the first joint portion 31 detected by the first joint angular sensor 14 and the joint angle of the second joint portion 32 detected by the second joint angular sensor 15, respectively.

In this example, the above-described operating unit 18 includes the operator (hereinafter described as a "computation instruction operator") of, for example, buttons, for a user to instruct an execution of the computation to determine the length of the surgical instrument 4, and the computing unit 10 performs the computation of the length Ls based on the above-described [Formula 1] in response to the operation input by this computation instruction operator.

In some embodiments, a user may operate the computation instruction operator in response to the positioning of the distal end of the surgical instrument 4 to the predetermined position Pt. This configuration guarantees that the length Ls is computed in response to the completion of the positioning of the distal end of the surgical instrument 4 to the predetermined position Pt, thereby achieving an improved measurement accuracy of the length Ls.

Figure 7:
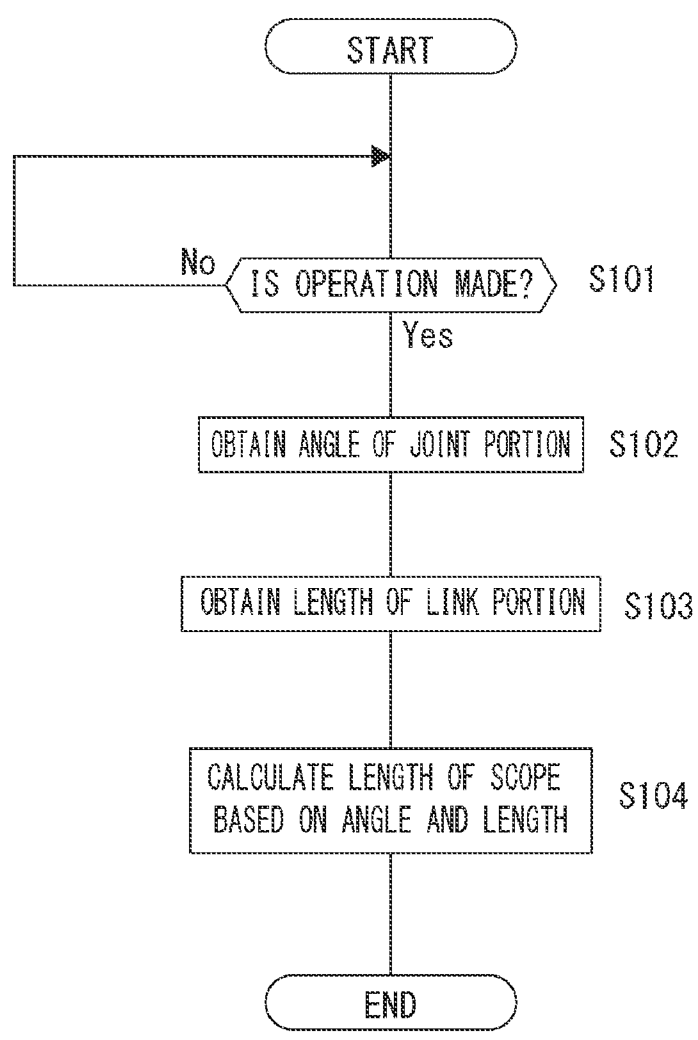
FIG. 7 is a flowchart illustrating a specific processing procedure example for achieving the computation method of the length of the surgical instrument, according to some embodiments.

FIG. 7 is a flowchart illustrating a specific processing procedure example for achieving the computation method of the length of the surgical instrument 4 according to some embodiments.

First, the computing unit 10 performs the process of standing by for the operation input by the computation instruction operator described above as an operation standby process at Step S101.

When the operation input by the computation instruction operator is made, the computing unit 10 proceeds the process to Step S102 to perform the process of obtaining the angles of the joint portions. Specifically, in this example, the process of obtaining the joint angle of the first joint portion 31 detected by the first joint angular sensor 14 and the joint angle of the second joint portion 32 detected by the second joint angular sensor 15 is performed.

At Step S103 subsequent to Step S102, the computing unit 10 performs the process of obtaining the length L1 of the first link portion 35 and the length L2 of the second link portion 36, which are known values, as the process of obtaining the lengths of the link portions. For example, the information on these lengths L1 and L2 is stored in a memory readable by the computing unit 10, and the computing unit 10 reads and obtains the information on these lengths L1 and L2 stored in the memory in the process of Step S103.

At Step S104 subsequent to Step S103, the computing unit 10 calculates a length of the scope based on the angles and the lengths. Specifically, the angle θ1 and the angle θ2 are determined based on the joint angle of the first joint portion 31 and the joint angle of the second joint portion 32, respectively, obtained at Step S102 and the computation based on the above-described [Formula 1] using these angles θ1 and θ2 and lengths L1 and L2 obtained at Step S103 is performed, and thus, the length Ls of the surgical instrument 4 as the scope is determined.

The computing unit 10 terminates the sequence of process illustrated in FIG. 7 in response to the execution of the process of Step S104.

In some embodiments, a guide light Li for positioning the distal end of the surgical instrument 4 at the predetermined position Pt may be used.

Note that, in the following description, the description is omitted for the portions similar to the portions that have already been described so far by attaching the same reference numerals. That is, repeated descriptions of like elements are omitted for conciseness.

Figure 8A:
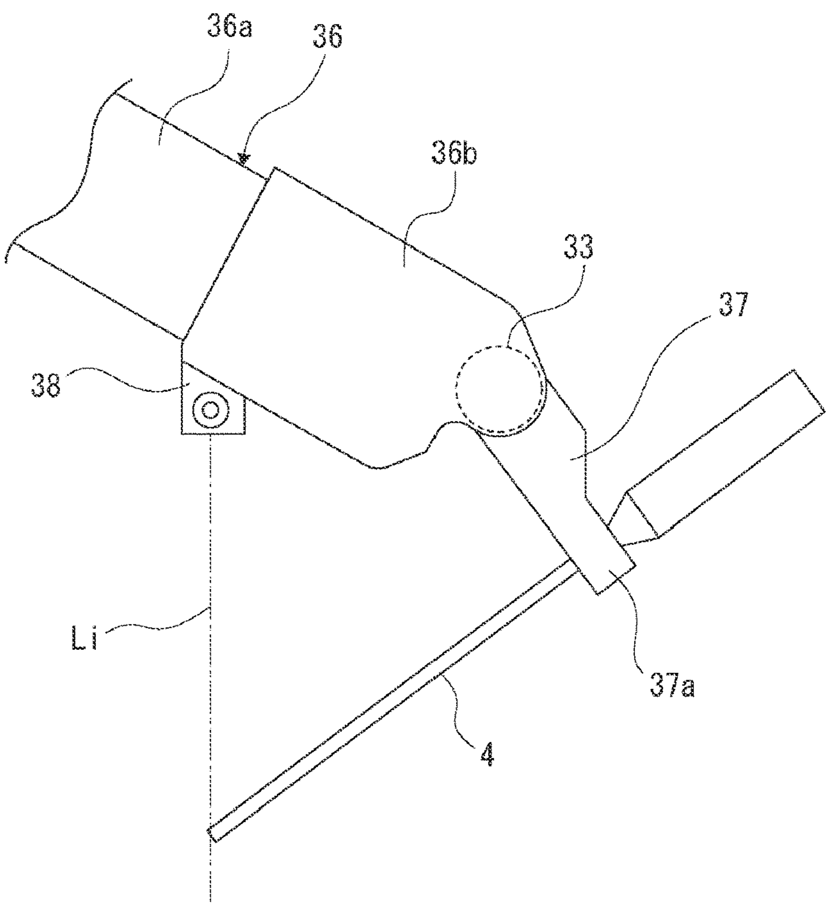
FIGS. 8A and 8B are drawings for describing a configuration of a surgery assisting device, according to some embodiments.
Figure 8B:
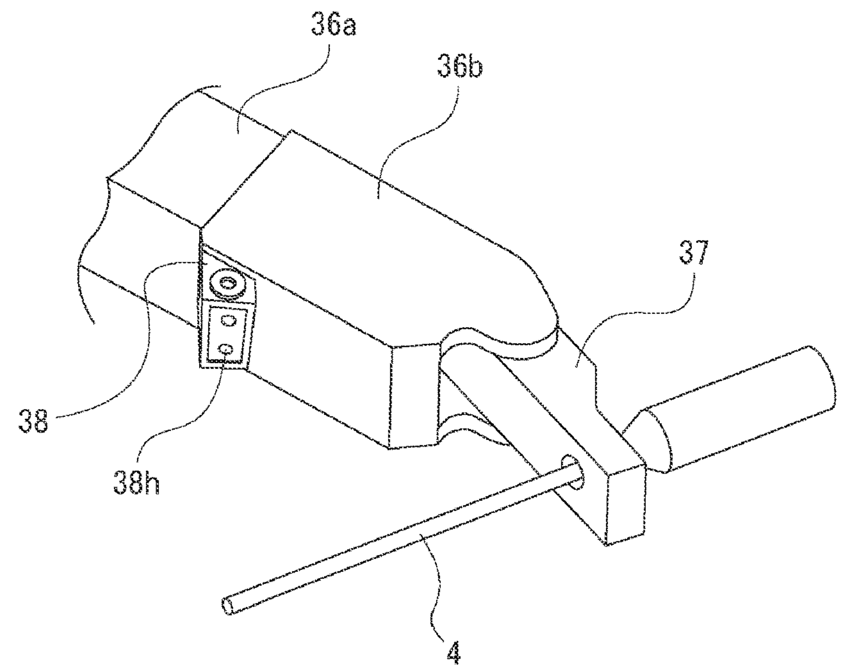

FIGS. 8A and 8B are drawings for describing a configuration of a surgery assisting device 1A according to some embodiments, and FIG. 8A extracts and illustrates only a portion of the arm distal end side from the second link portion 36 in the arm portion 3. Note that, the configuration of the portion in the arm base side with respect to the second link distal portion 36*b* in the arm portion 3 and the configurations other than the arm portion 3 are similar to those of the surgery assisting device 1 described above, and therefore, illustrations of these components are omitted for conciseness.

A difference from the surgery assisting device 1 described above is that a light emitting portion 38 that emits the above-described guide light Li is disposed in the second link distal portion 36*b*. As illustrated, the light emitting portion 38 is disposed on a lower surface side of the second link distal portion 36*b* and emits the guide light Li toward an outward direction of the second link distal portion 36*b*. FIG. 8B illustrates a state where the light emitting portion 38 is observed diagonally from the lower side of the second link distal portion 36*b*, and as illustrated, the light emitting portion 38 has a hole portion 38*h* and is configured to emit the guide light downward from the hole portion 38*h*.

In this example, the light emitting portion 38 has a laser 38*a* (not illustrated in FIG. 8) as a light source, thereby emitting the laser light as the guide light Li.

Figure 9:
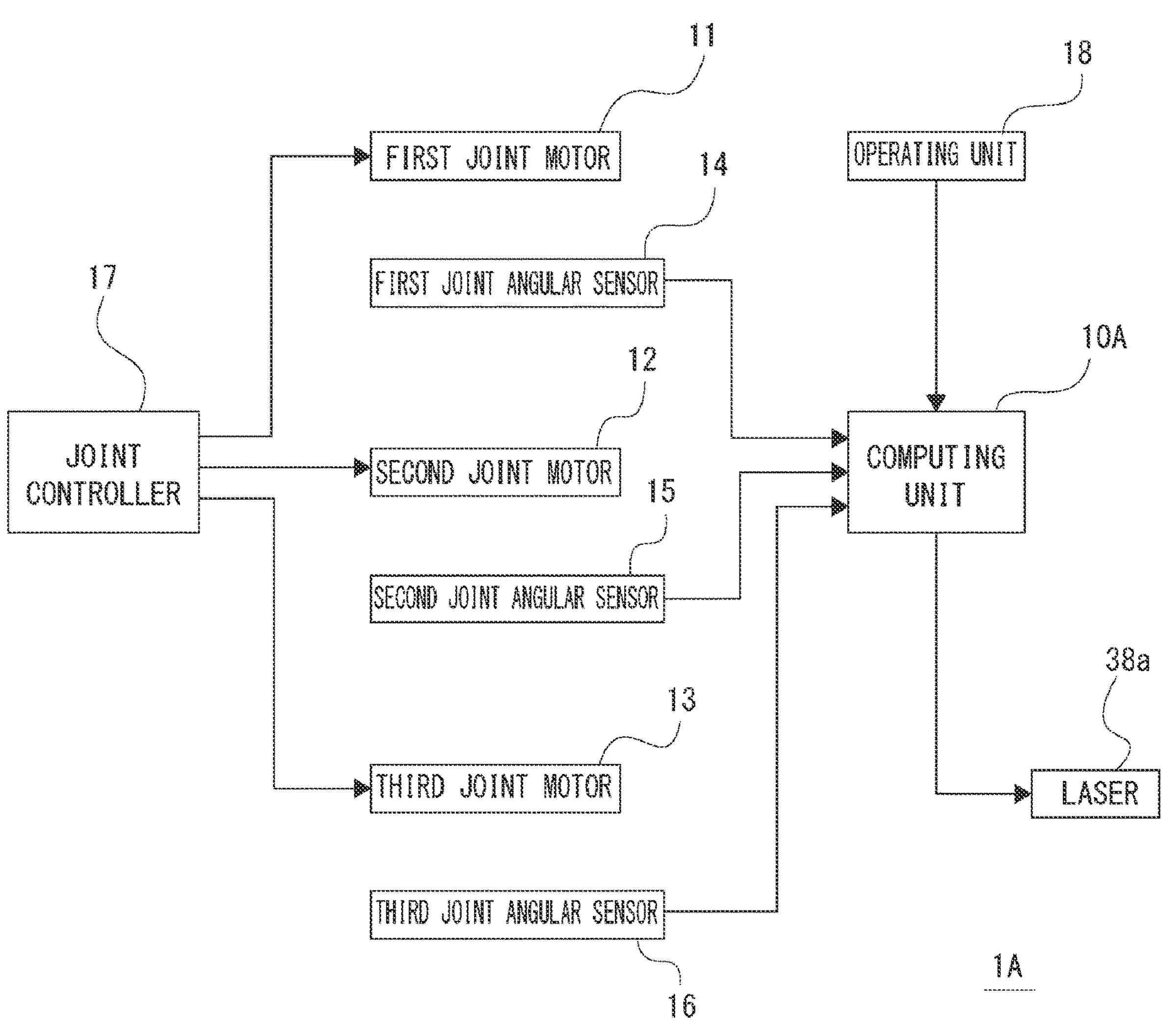
FIG. 9 is a block diagram illustrating an exemplary schematic internal configuration of the surgery assisting device, according to some embodiments.

FIG. 9 is a block diagram illustrating an exemplary schematic internal configuration of the surgery assisting device 1A according to some embodiments.

The differences from the surgery assisting device 1 described above are that the laser 38*a* in the light emitting portion 38 is disposed and a computing unit 10A is disposed instead of the computing unit 10.

The computing unit 10A determines the length Ls of the surgical instrument 4 by a method different from that of the computing unit 10 as described later. The computing unit 10A is configured to be able to control turning on and off of the laser 38*a*.

Figure 10:
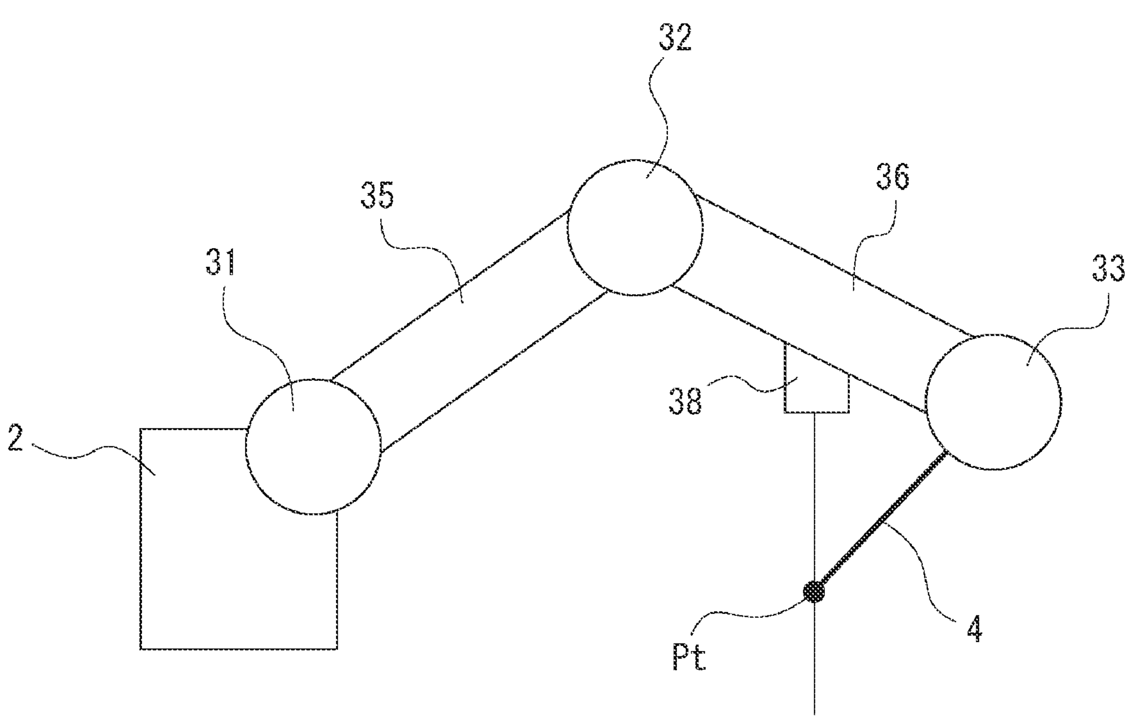
FIG. 10 is a drawing schematically illustrating a configuration of the surgery assisting device, according to some embodiments.

FIG. 10 is a drawing schematically illustrating a configuration of the surgery assisting device 1A according to some embodiments, and specifically, schematically illustrates a relationship between the first joint portion 31, the second joint portion 32, the third joint portion 33, the first link portion 35, and the second link portion 36, and the surgical instrument 4 in the surgery assisting device 1A.

In some embodiments, in determining the length of the surgical instrument 4, first, a user is caused to operate a predetermined operator (referred to as a first predetermined operator) in the operating unit 18. In response to the operation of this first predetermined operator, the computing unit 10A causes the light emitting portion 38 (the laser 38*a*) to emit the guide light Li.

The user manually operates the arm portion 3 (mainly an angle adjustment operation of the surgical instrument holding portion 37) in the state where the guide light Li is thus emitted to position the distal end of the surgical instrument 4 to the position where the guide light Li guides. Specifically, the distal end of the surgical instrument 4 is positioned to the position where it overlaps with the guide light Li as the laser light. In this example, the position of the distal end of the surgical instrument 4 in the state where the distal end of the surgical instrument 4 overlaps with the guide light Li is thus the predetermined position Pt.

Furthermore, the user operates a predetermined operator (referred to as a second predetermined operator) in the operating unit 18 in the state where the distal end of the surgical instrument 4 is positioned at the predetermined position Pt where the guide light Li guides as described above.

In response to the operation of the second predetermined operator, the computing unit 10A performs a computation to determine the length of the surgical instrument 4 by the method described below.

Note that the above-described first predetermined operator and second predetermined operator may be different operators or may be the same operator, according to various embodiments.

Figure 11:
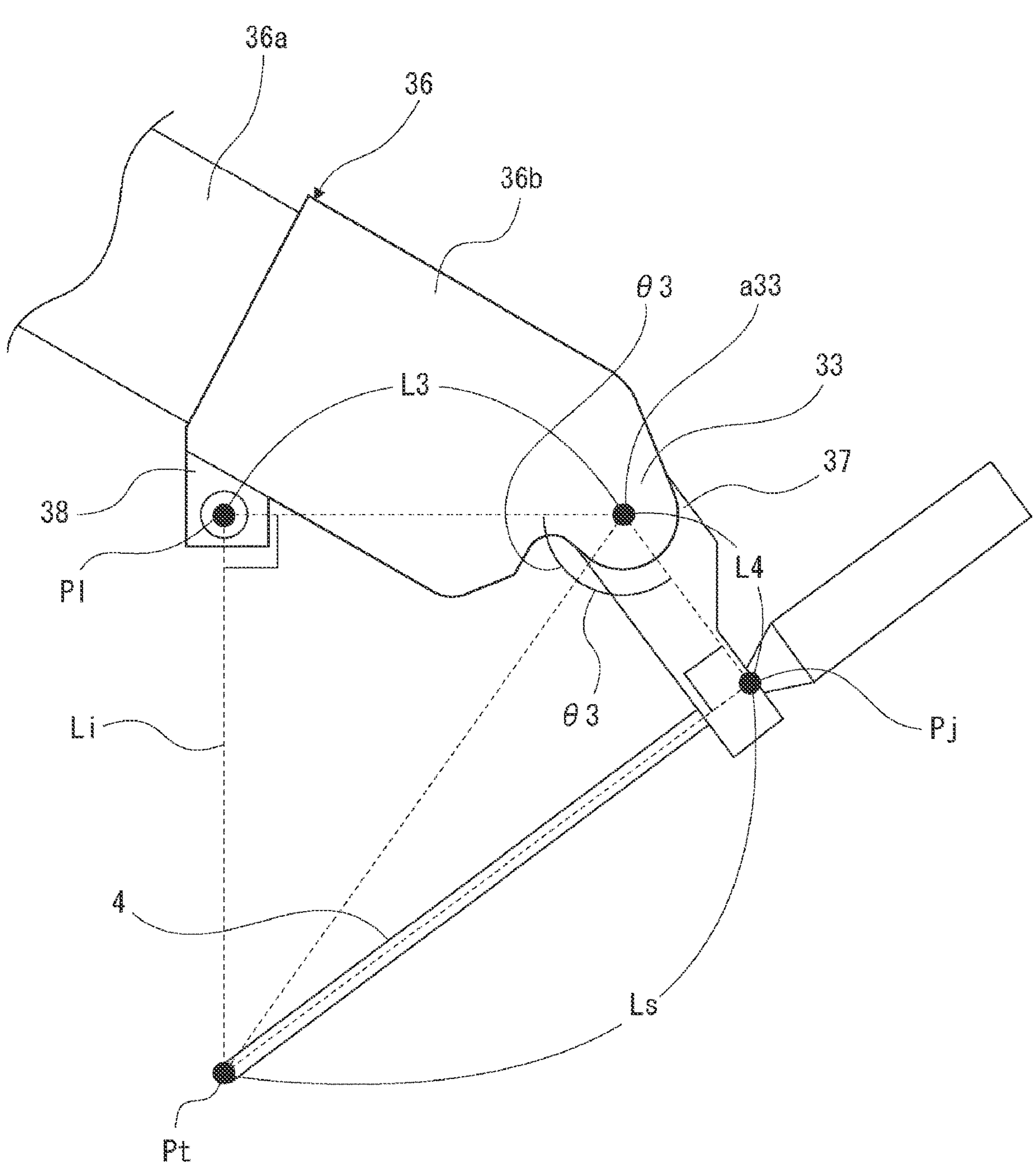
FIG. 11 is an explanatory drawing for a computation method of a length of the surgical instrument, according to some embodiments.

FIG. 11 is an explanatory drawing for the computation method of the length of the surgical instrument 4 according to some embodiments, and illustrates a relationship between the joint shaft a33 of the third joint portion 33, a point P1 as an intersection point between the perpendicular line drawn with respect to an optical axis of the guide light Li from the joint shaft a33 and the optical axis, a point Pj as an intersection point between the perpendicular line drawn with respect to a center axis of the surgical instrument 4 (which is a scope in this example too) from the joint shaft a33 and the center axis, and the predetermined position Pt (the position of the distal end in the state where the distal end of the surgical instrument 4 overlaps with the guide light Li in this example).

The point Pj, that is, the intersection point between the perpendicular line drawn with respect to the center axis of the surgical instrument 4 from the joint shaft a33 (the joint shaft of the distal end joint portion) and the center axis is a point adjacent to the point of holding the surgical instrument 4 by the surgical instrument holding portion 37, which can be a base position of the surgical instrument 4 in other words.

As illustrated, the angle formed by the straight line connecting the joint shaft a33 to the point P1 and the straight line connecting the joint shaft a33 to the point Pj is "θ3." The length of the straight line connecting the joint shaft a33 to the point P1 is "L3," and the length of the straight line connecting the joint shaft a33 to the point Pj (the base position) is "L4."

The angle θ3 can be determined based on the joint angle of the third joint portion 33 detected by the third joint angular sensor 16. The lengths L3 and L4 are lengths that do not change even when the third joint portion 33 is driven and are known lengths.

In some embodiments, the length Ls of the surgical instrument 4 may be determined by performing the computation shown in [Formula 2] below.

$$Ls = \frac{L4 \cdot \cos(\pi - \theta 3) + L3}{\sin(\pi - \theta 3)} \quad \text{[Formula 2]}$$

Figure 12:
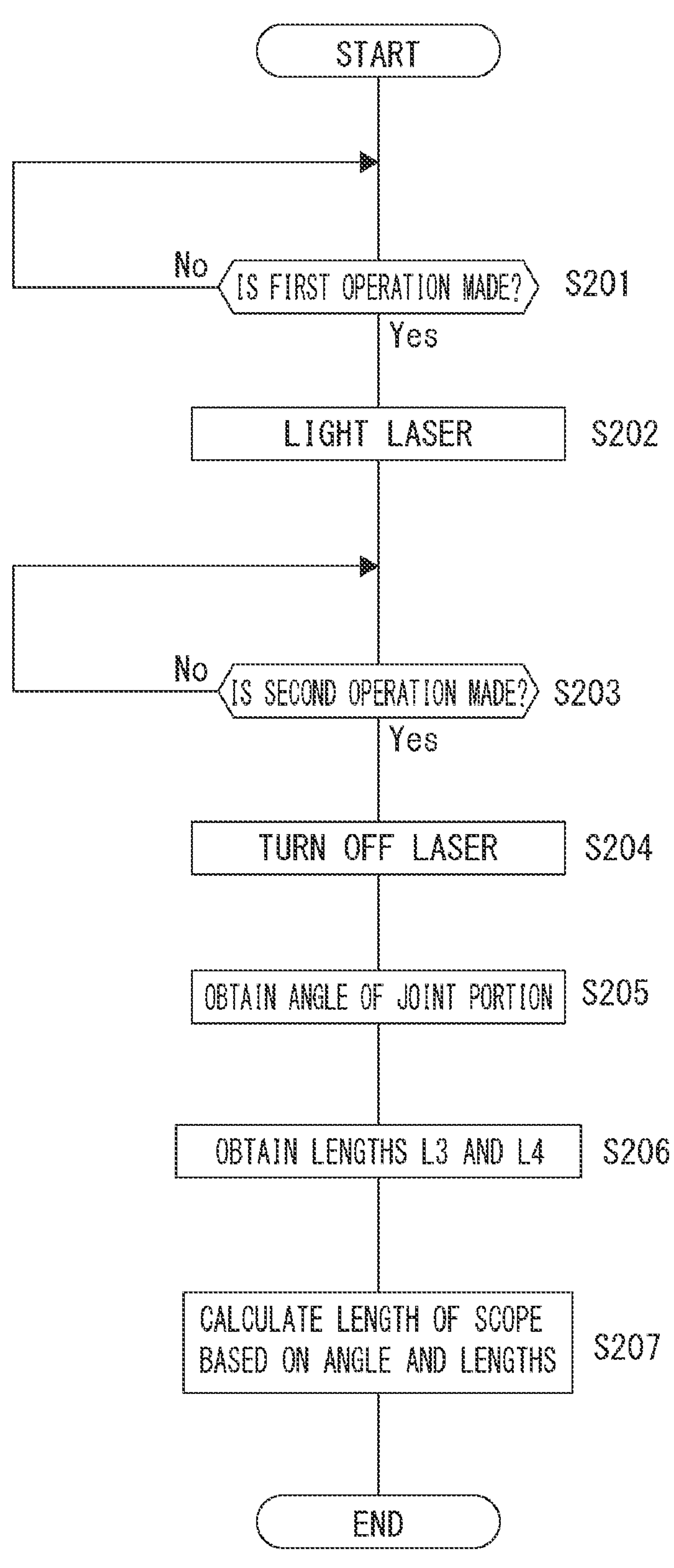
FIG. 12 is a flowchart illustrating a specific processing procedure example for achieving the computation method of the length of the surgical instrument, according to some embodiments.

FIG. 12 is a flowchart illustrating a specific processing procedure example for achieving the computation method of the length of the surgical instrument 4 according to some embodiments.

In FIG. 12, the computing unit 10A performs the process of standing by for an operation to the first predetermined operator described above as a stand-by process of the first operation at Step S201.

When the operation to the first predetermined operator is made, the computing unit 10A proceeds the process to Step S202 to perform the process of laser lighting. That is, the guide light Li is emitted by lighting the laser 38*a*.

At Step S203 subsequent to Step S202, the computing unit 10A performs the process of standing by for an operation to the second predetermined operator described above as a stand-by process of the second operation, and when the operation to the second predetermined operator is made, proceeds the process to Step S204 to perform a laser turning-off process, that is, the process of turning off the laser 38*a*.

At Step S205 subsequent to Step S204, the computing unit 10A performs the process of obtaining the angle of the joint portion. Specifically, the process of obtaining the joint angle of the third joint portion 33 detected by the third joint angular sensor 16 is performed.

At Step S206 subsequent to Step S205, the computing unit 10A performs, for example, the process of obtaining information on the length L3 and the length L4 as the known value stored in, for example, the memory as the process of obtaining the lengths L3 and L4.

At Step S207 subsequent to Step S206, the computing unit 10A calculates the length of the scope based on the angle and the length. That is, the angle θ3 is determined based on the joint angle of the third joint portion 33 obtained at Step S205 and the computation by the above-described [Formula 2] using this angle θ3 and the lengths L3 and L4 obtained by Step S206 is performed, thereby determining the length Ls of the surgical instrument 4 as the scope.

The computing unit 10A terminates the sequence of process illustrated in FIG. 12 in response to the execution of the process of Step S207.

<Modifications>

Note that the embodiments are not limited to the specific examples described above, and may employ configurations as various modifications.

For example, the example in which the predetermined position Pt is a position in air has been described above, but the predetermined position Pt can be set at a predetermined position in the surgery assisting device 1.

Figure 13:
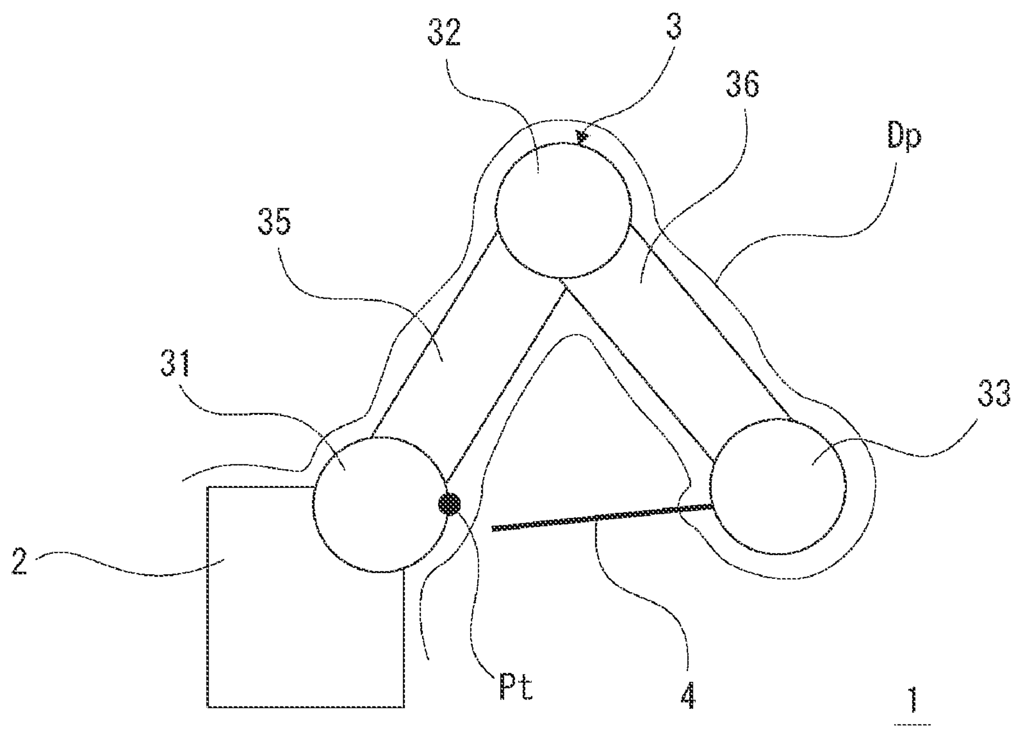
FIG. 13 is an explanatory drawing for a modification according to a setting of a predetermined position, according to some embodiments.

For example, the predetermined position Pt can be set in the base portion of the arm portion 3, specifically, on a surface opposable to the distal end of the surgical instrument 4 in the first joint portion 31, as exemplarily illustrated in FIG. 13. It is needless to say that the predetermined position Pt is set at the position where the distal end of the surgical instrument 4 can be brought into contact by the bending movement of the arm portion 3 at this time.

The surface of the surgery assisting device 1 is not, for example, specifically sterilized and is an area sectioned as what is called an unclean area. In view of this situation, setting the predetermined position Pt at any position on the surgery assisting device 1, that is, directly bringing the distal end of the surgical instrument 4 into contact with the surgery assisting device 1 when the length Ls is determined as described above is not advantageous in a sense that the surgical instrument 4 cannot be kept clean.

Therefore, when the predetermined position Pt is set at any position on the surgery assisting device 1, the predetermined position Pt may advantageously be set at a position covered by a drape (a sterile drape) Dp in the surgery assisting device 1 (see FIG. 13).

This configuration ensures bringing the distal end of the surgical instrument 4 into contact with the surgery assisting device 1 over the sterilized drape Dp when the length Ls of the surgical instrument 4 is determined.

Accordingly, the prevention of the distal end of the surgical instrument 4 falling into an unclean state upon determining the length of the surgical instrument 4 is achieved, thereby ensuring increased medical safety.

While the description has been made so far on the premise that a user is caused to determine whether the distal end of the surgical instrument 4 is positioned at the predetermined position Pt or not when the length Ls is determined, it is also possible to provide a configuration in which the determination of whether the distal end of the surgical instrument 4 is positioned at the predetermined position Pt or not based on, for example, captured images by a camera.

In the example of using the guide light Li like the second embodiment, it is also possible to provide a configuration that determines whether the distal end of the surgical instrument 4 is positioned at the predetermined position Pt or not by detecting a change in amount of light generated by the distal end of the surgical instrument 4 overlapping with the guide light Li, such as detecting that the light beam of the guide light Li is obstructed by the distal end of the surgical instrument 4.

Furthermore, when the configuration that determines whether the distal end of the surgical instrument 4 is positioned at the predetermined position Pt or not is provided like these examples, it is also possible to provide a configuration that performs the computation of the length Ls in response to the determination that the distal end of the surgical instrument 4 is positioned at the predetermined position Pt.

While the description has been made above on the premise that a user manually moves the arm portion 3 to position the distal end of the surgical instrument 4 at the predetermined position Pt, the positioning of the distal end of the surgical instrument 4 to the predetermined position Pt can be automatically performed by a control by the joint controller 17.

Furthermore, while the description has been made above with the example in which the computation of the length Ls of the surgical instrument 4 is performed by the surgery assisting device, it is also possible to provide a configuration in which an external unit of the surgery assisting device, such as the master device 20, performs the computation of the length Ls based on the information on the joint angle and the like obtained from a side of the surgery assisting device. In this case, the external unit, such as the master device 20, corresponds to the computing device according to some embodiments.

While the description has been made above with the example in which the length of the surgical instrument is determined by performing a computation based on the trigonometric function, it is also possible to, for example, determine coordinates of representative points of, for example, the joint shafts based on the joint angles in the state where the distal end of the surgical instrument is positioned at the predetermined position and the information on the known lengths, such as the lengths of the link portions to determine the length of the surgical instrument by, for example, a matrix calculation using the coordinates of the representative points. That is, obtaining at least the angle information of the joint portion ensures determining the length of the surgical instrument by a geometric computation using the angle information.

As described above, a computing device (the surgery assisting device 1, 1A) according to some embodiments, for a surgery assisting device that is configured to hold a surgical instrument on a distal end portion and includes a freely bendable arm portion by including one or more joint portions, includes a computing unit (the computing unit 10, 10A) that obtains angle information of at least one joint portion of the one or more joint portions in a state where a distal end of the surgical instrument held by the arm portion is positioned at a predetermined position (the predetermined position Pt) and determines a length of the surgical instrument by a geometric computation using the angle information.

When the condition that the distal end of the surgical instrument is positioned at the predetermined position is imposed, the angles of the joint portions also change if the length of the surgical instrument differs. Therefore, under the condition that the distal end of the surgical instrument is positioned at the predetermined position as described above, it is possible to appropriately determine the length of the surgical instrument by the geometric computation by obtaining the angle information of the joint portions.

By being able to determine the length of the surgical instrument, it is possible to allow the use even of the surgical instrument with an unknown length, thereby ensuring an improved degree of freedom of the usable surgical instrument. Since it is not necessary to use a jig for keeping the length of the surgical instrument constant, it is possible to avoid the labor relating to sterilize the jig and a cost increase when the jig is discarded after each use.

In the computing device according to some embodiments, the predetermined position may be a position in air.

This configuration eliminates the need for bringing the distal end of the surgical instrument into contact with an object in determining the length of the surgical instrument.

Accordingly, the distal end of the surgical instrument can be kept clean, thereby ensuring increased medical safety.

Furthermore, in the computing device according to some embodiments, as the one or more joint portions, a first joint portion (the first joint portion 31), a second joint portion (the second joint portion 32), and a third joint portion (the third joint portion 33) are arranged in order from a base side to a distal end side of the arm portion, and the computing unit (the computing unit 10) determines the length of the surgical instrument by: obtaining angle information (the angle θ1) of the first joint portion and angle information (the angle θ2) of the second joint portion in a state where the distal end of the surgical instrument is positioned at the predetermined position; and performing a computation based on a trigonometric function using the obtained angle information of the first joint portion and angle information of the second joint portion, a length (the length L1) of a link portion between the first joint portion and the second joint portion, and a length (the length L2) of a link portion between the second joint portion and the third joint portion.

This configuration ensures determining the length of the surgical instrument corresponding to the case where the arm portion includes three or more joint portions.

Furthermore, in the computing device according to some embodiments, the arm portion includes a surgical instrument holding portion (the surgical instrument holding portion 37) positioned at a distal end portion of the arm portion and configured to hold the surgical instrument, a distal end joint portion (the third joint portion 33) as the joint portion to which the surgical instrument holding portion is coupled, and a light emitting portion (the light emitting portion 38) disposed in a link portion (the second link portion 36) in an arm base side of the distal end joint portion and emits a guide light that guides a position of the distal end of the surgical instrument toward an outward direction of the link portion, the computing unit (the computing unit 10A) determines the length of the surgical instrument by obtaining angle information (the angle θ3) of the distal end joint portion in a state where the distal end of the surgical instrument is positioned at the position where the guide light guides and performing a geometric computation using the angle information.

Since the distal end of the surgical instrument is guided which position to be positioned for determining the length of the surgical instrument, it is easy for a user to adjust the distal end position of the surgical instrument to the predetermined position.

Accordingly, an improvement in positioning accuracy of the distal end position of the surgical instrument is achieved, thereby ensuring an achievement of improved measurement accuracy of the length of the surgical instrument.

In the computing device according to some embodiments, the computing unit determines the length of the surgical instrument by performing a computation based on a trigonometric function using the obtained angle information of the distal end joint portion, a length (the length L3) of a perpendicular line to an optical axis of the guide light from a joint shaft (the joint shaft a33) of the distal end joint portion, and a length (the length L4) from the joint shaft of the distal end joint portion to a base position of the surgical instrument.

This configuration ensures appropriately determining the length of the surgical instrument when the method of emitting the guide light from the light emitting portion disposed in the link portion in the arm base side of the distal end joint portion is employed.

Furthermore, in the computing device according to some embodiments, the predetermined position is a position covered by the drape in the surgery assisting device (see FIG. 13).

This configuration ensures bringing the distal end of the surgical instrument into contact with the surgery assisting device over the sterilized drape when the length of the surgical instrument is determined.

Accordingly, the prevention of the distal end of the surgical instrument falling into an unclean state upon determining the length of the surgical instrument is achieved, thereby ensuring increased medical safety.

Furthermore, in the computing device according to some embodiments, the computing unit performs a computation to determine the length of the surgical instrument according to an operation to a predetermined operator disposed in the surgery assisting device.

The above-described predetermined operator can be functioned as an operator for notifying the device side of the completion of the positioning of the distal end of the surgical instrument to the predetermined position, and the above-described configuration ensures appropriately performing the computation to determine the length of the surgical instrument in response to the completion of the positioning.

Accordingly, an improvement in measurement accuracy of the length of the surgical instrument can be achieved.

It should be understood that the present disclosure is not limited to the above embodiments, but various other changes and modifications may be made therein without departing from the spirit and scope of the appended claims.

What is claimed is:

1. A surgery assisting device comprising:

an arm including one or more joint portions and configured to hold a surgical instrument;

one or more joint angular sensors configured to detect angle information of at least one joint portion of the one or more joint portions; and a processor configured to obtain the angle information from the one or more joint angular sensors in a state in which a distal end of the surgical instrument is positioned at a predetermined position, determine a length of the surgical instrument based on the angle information, and control the arm in accordance with the determined length.

2. The surgery assisting device according to claim 1, wherein the predetermined position is a position in air.

3. The surgery assisting device according to claim 1, wherein:

the one or more joint portions comprise a first joint portion, a second joint portion, and a third joint portion that are arranged in order from a base of the arm to a distal end of the arm, the arm further includes a first link portion linking the first joint portion to the second joint portion, and a second link portion linking the second joint portion to the third joint portion, the angle information comprises first angle information of the first joint portion and second angle information of the second joint portion in the state in which the distal end of the surgical instrument is positioned at the predetermined position; and the processor determines the length of the surgical instrument based on the first angle information, the second angle information, the length of the first link portion, and the length of the second link portion.

4. The surgery assisting device according to claim 1, wherein:

the one or more joint portions include a distal end joint portion, the arm further includes:

a surgical instrument holder that is coupled to the distal end joint portion and that is configured to hold the surgical instrument; and a light emitter that is disposed in a link portion at a proximal end of the distal end joint portion and that emits a guide light that guides a position of the distal end of the surgical instrument, and the angle information comprises angle information of the distal end joint portion in the state in which the distal end of the surgical instrument is positioned at the position indicated by the guide light.

5. The surgery assisting device according to claim 4, wherein:

the distal end joint portion includes a joint shaft, and the processor determines the length of the surgical instrument based on the angle information of the distal end joint portion, a length of a line perpendicular to an optical axis of the guide light from the joint shaft of the distal end joint portion, and a length from the joint shaft of the distal end joint portion to a base of the surgical instrument.

6. The surgery assisting device according to claim 1, further comprising a drape, wherein the predetermined position is a position covered by the drape.

7. The surgery assisting device according to claim 1, further comprising an input device, wherein the processor determines the length of the surgical instrument in response to an operation input to the input device.

8. The surgery assisting device according to claim 1, wherein the predetermined position is a position known in advance.

9. The computing device according to claim 1, wherein the arm further comprises two or more link portions connected to the one or more joint portions, and wherein the computing device is configured to determine the length of the surgical instrument based on the angle information and respective lengths of each of the two or more link portions.

10. A computing device for a surgery assisting device that is configured to hold a surgical instrument on a distal end portion of the surgery assisting device and that includes an arm portion including one or more joint portions and one or more joint angular sensors configured to detect angle information of at least one joint portion of the one or more joint portions, the computing device comprising:

a microcomputer that obtains the angle information from the one or more joint angular sensors in a state in which a distal end of the surgical instrument held by the arm portion is positioned at a predetermined position, that determines a length of the surgical instrument by based on the angle information, and that controls the arm portion in accordance with the determined length.

11. The computing device according to claim 10, wherein the predetermined position is a position in air.

12. The computing device according to claim 11, wherein:

the one or more joint portions comprise a first joint portion, a second joint portion, and a third joint portion that are arranged in order from a base side to a distal end side of the arm portion, and the angle information includes first angle information of the first joint portion and second angle information of the second joint portion in the state in which the distal end of the surgical instrument is positioned at the predetermined position, and the microcomputer determines the length of the surgical instrument based on the first angle information, the second angle information, a length of a link portion between the first joint portion and the second joint portion, and a length of a link portion between the second joint portion and the third joint portion.

13. The computing device according to claim 10, wherein:

the one or more joint portions comprise a first joint portion, a second joint portion, and a third joint portion that are arranged in order from a base side to a distal end side of the arm portion, and the angle information includes first angle information of the first joint portion and second angle information of the second joint portion in the state in which the distal end of the surgical instrument is positioned at the predetermined position; and the microcomputer determines the length of the surgical instrument based on the first angle information, the second angle information, a length of a link portion between the first joint portion and the second joint portion, and a length of a link portion between the second joint portion and the third joint portion.

14. The computing device according to claim 10, wherein:

the one or more joint portions include a distal end joint portion, the arm portion further includes:

a surgical instrument holding portion that is positioned at a distal end portion of the arm portion and that is configured to hold the surgical instrument, the surgical instrument holding portion being coupled to the distal end joint portion; and a light emitting portion that is disposed in a link portion at an arm base side of the distal end joint portion and that emits a guide light that guides a position of the distal end of the surgical instrument toward an outward direction of the link portion, and the angle information includes angle information of the distal end joint portion in a state in which the distal end of the surgical instrument is positioned at the position at which the guide light guides, and the microcomputer determines the length of the surgical instrument based on the angle information of the distal end joint portion.

15. The computing device according to claim 10, wherein the predetermined position is a position covered by a drape in the surgery assisting device.

16. The computing device according to claim 10, wherein the microcomputer determines the length of the surgical instrument in response to an operation to a predetermined input device disposed in the surgery assisting device.

17. The computing device according to claim 10, wherein the predetermined position is a position known in advance.

18. The computing device according to claim 10, wherein the arm further comprises two or more link portions connected to the one or more joint portions, and wherein the computing device is configured to determine the length of the surgical instrument based on the angle information and respective lengths of each of the two or more link portions.

19. A computing device for a surgery assisting device that is configured to hold a surgical instrument on a distal end portion of the surgery assisting device and that includes an arm portion including one or more joint portions and one or more joint angular sensors configured to detect angle information of at least one joint portion of the one or more joint portions, the computing device comprising:

a microcomputer that obtains the angle information from the one or more joint angular sensors in a state in which a distal end of the surgical instrument held by the arm portion is positioned at a predetermined position, that determines a length of the surgical instrument by based on the angle information, and that controls the arm portion based on the determined length, wherein:

the one or more joint portions include a distal end joint portion, the arm portion further includes:

a surgical instrument holding portion that is positioned at a distal end portion of the arm portion and that is configured to hold the surgical instrument, the surgical instrument holding portion being coupled to the distal end joint portion; and a light emitting portion that is disposed in a link portion at an arm base side of the distal end joint portion and that emits a guide light that guides a position of the distal end of the surgical instrument toward an outward direction of the link portion, the predetermined position is the position at which the guide light guides, and the microcomputer determines the length of the surgical instrument based on angle information of the distal end joint portion.

20. The computing device according to claim 19, wherein the microcomputer determines the length of the surgical instrument based on the angle information of the distal end joint portion, a length of a perpendicular line to an optical axis of the guide light from a joint shaft of the distal end joint portion, and a length from the joint shaft of the distal end joint portion to a base position of the surgical instrument.

* * * * *